US010591475B2

(12) United States Patent
Tischer (10) Patent No.: US 10,591,475 B2
(45) Date of Patent: Mar. 17, 2020

(54) RESONATOR SENSOR MODULE SYSTEM AND METHOD

(71) Applicant: QORVO US, INC., Greensboro, NC (US)

(72) Inventor: John Mark Tischer, Waseca, MN (US)

(73) Assignee: QORVO BIOTECHNOLOGIES, LLC, Plymouth, MN (US)

( * ) Notice: Subject to any disclaimer, the term of this patent is extended or adjusted under 35 U.S.C. 154(b) by 0 days.

(21) Appl. No.: 16/575,607

(22) Filed: Sep. 19, 2019

(65) Prior Publication Data

US 2020/0011863 A1    Jan. 9, 2020

Related U.S. Application Data

(62) Division of application No. 14/893,404, filed as application No. PCT/US2014/039291 on May 23, 2014, now Pat. No. 10,451,618.

(60) Provisional application No. 61/826,920, filed on May 23, 2013.

(51) Int. Cl.
*G01N 33/543* (2006.01)
*G01N 33/557* (2006.01)

(52) U.S. Cl.
CPC ..... *G01N 33/54373* (2013.01); *G01N 33/557* (2013.01)

(58) Field of Classification Search
None
See application file for complete search history.

(56) References Cited

U.S. PATENT DOCUMENTS

| | | | |
|---|---|---|---|
| 2,136,612 | A | 11/1938 | Dubuar |
| 2,881,273 | A | 4/1959 | Shaler |
| 2,951,218 | A | 8/1960 | Arditi |
| 4,634,195 | A | 1/1987 | Shoemaker |
| 5,554,042 | A | 9/1996 | Denninger |
| 5,910,522 | A | 6/1999 | Schmidt et al. |
| 5,932,953 | A | 8/1999 | Drees et al. |
| 6,055,448 | A | 4/2000 | Anderson et al. |
| 6,093,059 | A | 7/2000 | Bogese |
| 6,237,417 | B1 | 5/2001 | Lonsdale et al. |
| 6,467,351 | B2 | 10/2002 | Lonsdale et al. |
| 6,551,128 | B2 | 4/2003 | Asai |
| 6,623,307 | B2 | 9/2003 | Korsunsky et al. |

(Continued)

FOREIGN PATENT DOCUMENTS

WO    WO 2014/190238 A1    11/2014
WO    WO 2014/190295 A3    11/2014

OTHER PUBLICATIONS

European Patent Application No. 14800271.0, filed May 23, 2014; Supplementary Search Report dated Dec. 9, 2016; 10 pages.

(Continued)

*Primary Examiner* — Rebecca L Martinez
(74) *Attorney, Agent, or Firm* — Mueting, Raasch & Gebhardt, P.A.

(57) ABSTRACT

A resonator sensor module is disclosed. The resonator sensor module includes one or more sensing resonators that includes binding sites for an analyte material; one or more reference resonators that lacks any binding sites for the analyte material; a module interface; and one or more switches each including a first position that operatively couples at least one of the one or more sensing resonators and the module interface and a second position that operatively couples at least one of the one or more reference resonators and the module interface.

6 Claims, 6 Drawing Sheets

(56) References Cited

U.S. PATENT DOCUMENTS

| | | | |
|---|---|---|---|
| 7,349,223 B2 | 3/2008 | Haemer et al. |
| 7,563,128 B2 | 7/2009 | Suzuki et al. |
| 7,621,761 B2 | 11/2009 | Mok et al. |
| 7,690,923 B2 | 4/2010 | Horchler et al. |
| 7,721,590 B2 | 5/2010 | Kolosov et al. |
| 7,933,123 B2 | 4/2011 | Wang et al. |
| 8,178,047 B2 | 5/2012 | Wang et al. |
| 8,333,619 B2 | 12/2012 | Kondo et al. |
| 8,346,482 B2 | 1/2013 | Fernandez |
| 8,409,875 B2 | 4/2013 | Johal et al. |
| 8,441,081 B2 | 5/2013 | Arora et al. |
| 2002/0123270 A1 | 9/2002 | Belopolsky |
| 2003/0101006 A1 | 5/2003 | Mansky et al. |
| 2005/0042931 A1 | 2/2005 | Lavie |
| 2005/0227508 A1 | 10/2005 | Syms |
| 2006/0133952 A1 | 6/2006 | Zhang et al. |
| 2006/0134362 A1 | 6/2006 | Lu et al. |
| 2006/0242828 A1 | 11/2006 | Kirby et al. |
| 2010/0021346 A1 | 1/2010 | Wakamatsu et al. |
| 2010/0068933 A1 | 3/2010 | Ikegami et al. |
| 2011/0130048 A1 | 6/2011 | Haunberger et al. |
| 2011/0143601 A1 | 6/2011 | Katsui et al. |
| 2011/0190615 A1 | 8/2011 | Phillips et al. |
| 2012/0100636 A1 | 4/2012 | Johal et al. |
| 2012/0330179 A1 | 12/2012 | Yuk et al. |
| 2013/0018250 A1 | 1/2013 | Caprio et al. |
| 2013/0018251 A1 | 1/2013 | Caprio et al. |
| 2013/0045474 A1 | 2/2013 | Rozmyslowicz et al. |
| 2013/0068025 A1 | 3/2013 | Medin et al. |
| 2013/0084716 A1 | 4/2013 | Namjoshi et al. |
| 2013/0102199 A1 | 4/2013 | Venaleck et al. |
| 2013/0105984 A1 | 5/2013 | Rathburn |

OTHER PUBLICATIONS

International Search Report / Written Opinion dated Sep. 30, 2014, International Application No. PCT/US2014/039291, filed May 23, 2014; 10 pages.

International Search Report / Written Opinion dated Sep. 30, 2014, International Application No. PCT/US2014/039294, filed May 23, 2014; 10 pages.

International Preliminary Report on Patentability dated Dec. 3, 2015, International Application No. PCT/US2014/039291, filed May 23, 2014; 8 pgs.

International Preliminary Report on Patentability dated Dec. 3, 2015, International Application No. PCT/US2014/039294, filed May 23, 2014; 8 pgs.

Sauerbrey, *Zeitschrift für Physik*, 155(2):206-222.

RESONATOR SENSOR MODULE SYSTEM AND METHOD

This application is a divisional of U.S. patent application Ser. No. 14/893,404, titled RESONATOR SENSOR MODULE SYSTEM AND METHOD, filed Nov. 23, 2015 (pending), which is a U.S. National Stage Application of International Application No. PCT/US2014/039291, titled RESONATOR SENSOR MODULE AND SYSTEM AND METHOD USING SAME, filed on May 23, 2014, which claims the benefit of U.S. Provisional Application No. 61/826,920 filed May 23, 2013, entitled RESONATOR SENSOR MODULE AND SYSTEM AND METHOD USING SAME, the disclosures of which are incorporated by reference herein in their entirety.

FIELD

The present disclosure relates to measurement and testing, and more specifically to resonator sensors and associated apparatus for diagnostic measuring or testing in response to exposure of the sensors to certain materials.

BACKGROUND

Piezoelectric devices such as thin film bulk acoustic resonators (TFBAR) and similar technologies like quartz crystal microbalances (QCM) have been employed as mass detectors for some time. One application of piezoelectric resonators is in detecting very small quantities of materials. Piezoelectric resonators used as sensors in such applications are sometimes called "micro-balances." A piezoelectric resonator is typically constructed as a thin, planar layer of crystalline or polycrystalline piezoelectric material sandwiched between two electrode layers. When used as a sensor, the resonator is exposed to the material being detected to allow the material to bind on a surface of the resonator.

One conventional way of detecting the amount of the material bound on the surface of a resonator is to operate the resonator as an oscillator at its resonant frequency. As the material being detected binds on the resonator surface, the oscillation frequency of the resonator is reduced. This change in the oscillation frequency of the resonator, presumably caused by the binding of the material on the resonator surface, is measured and used to calculate the amount of the material bound on the resonator or the rate at which the material accumulates on the resonator's surface.

The sensitivity of a piezoelectric resonator in air as a material sensor is theoretically proportional to the square of the resonance frequency. See, e.g., G. Sauerbrey, *Zeitschrift für Physik* 155 (2): 206-222. Thus, the sensitivities of material sensors based on the popular quartz crystal resonators are limited by their relatively low oscillating frequencies, which typically range from several MHz to about 100 MHz. The development of thin-film resonator (TFR) technology can potentially produce sensors with significantly improved sensitivities. A thin-film resonator is formed by depositing a thin film of piezoelectric material, such as AN or ZnO, on a substrate. Due to the small thickness of the piezoelectric layer in a thin-film resonator, which is on the order of several microns, the resonant frequency of the thin-film resonator is on the order of 1 GHz. The high resonant frequencies and the corresponding high sensitivities make thin-film resonators useful for material sensing applications.

SUMMARY

In one aspect, the present disclosure provides a resonator sensor module that includes one or more sensing resonators that includes binding sites for an analyte material; one or more reference resonators that lacks any binding sites for the analyte material; a module interface; and one or more switches each including a first position that operatively couples at least one of the one or more sensing resonators and the module interface and a second position that operatively couples at least one of the one or more reference resonators and the module interface.

In some embodiments, the resonator sensor module can be included in a resonator sensor system for measuring binding kinetics of an interaction of an analyte material present in a fluid sample. The system also includes a measurement apparatus operatively coupled to the resonator sensor module through the module interface. The measurement apparatus includes actuation circuitry configured to drive the one or more sensing resonators and the one or more reference resonators into an oscillating motion; measurement circuitry configured to measure one or more resonator output signals representing a resonance characteristic of the oscillating motion of the one or more sensing resonators and the one or more reference resonators; and a controller operatively coupled to the actuation and measurement circuitry.

In another aspect, the present disclosure provides a method for measuring binding kinetics of an interaction of an analyte material present in a fluid sample. The method includes providing a resonator sensor module including one or more sensing resonators, one or more reference resonators, a module interface, and a switch. The one or more sensing resonators includes binding sites for the analyte material and the one or more reference resonators lacks any binding sites for the analyte. The method further includes positioning the switch in a first position such that the one or more sensing resonators is operatively coupled to the module interface. Prior to exposing the one or more sensing resonators and the one or more reference resonators to the fluid sample, the method includes initiating operation of the one or more sensing resonators via the module interface such that the one or more sensing resonators produces at least one sensor output signal representing a resonance characteristic of the one or more sensing resonators. The method further includes automatically detecting introduction of a fluid sample to the one or more sensing resonators based on detection of a characteristic change in the at least one sensor output signal; positioning the switch in a second position such that the one or more reference resonators is operatively coupled to the module interface; and initiating operation of the one or more reference resonators via the module interface such that the one or more reference resonators produces at least one reference output signal representing a resonance characteristic of the one or more reference resonators. In response to the detecting of the introduction of the fluid sample, the method includes initiating automated measurement of the binding kinetics of the analyte material to the one or more sensing resonators.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure describes various embodiments of resonator sensor modules that, in some embodiments, include one or more switches that are configured to select between two or more resonator sensors. In some embodiments, one or more switches are used to select between one or more sensing resonators and one or more reference resonators. Further, in some embodiments, the one or more switches can be integrated into a resonator sensor module.

A resonator sensor module that includes a switch can provide several advantages. For example, actuation and measurement circuitry of a resonator sensor system that is designed to interface with the resonator sensor module can be simplified by requiring a single set of actuation and measurement circuitry to drive and measure two or more resonators. The implementation of a switch within the resonator sensor module can also increase the accuracy of differential resonator measurements, where even small differences in multiple measurement circuits can create significant errors in the measured values. Further, one or more switches can also improve the accuracy of making differential resonator measurements at high resonant frequencies, where even small differences in the electrical connectivity to the two or more resonators can create significant errors in the measured values. These differences in electrical connectivity can be caused by temperature differences in the connections between the actuation and measurement circuitry and the resonators, or changes in the connectivity between the actuation and measurement circuitry and the resonators cause by normal wear or contamination from the operating environment. One or more switches can also be used to verify electrical connectivity and instrumentation accuracy. In summary, the use of one or more switches in the described resonator sensor modules can provide a more robust and reliable connection to a measurement apparatus, thereby providing more accurate measurements in real-world usage environments.

Turning now to the drawings, the components of various embodiments of resonator sensor modules, and systems and methods that utilize such modules are illustrated. In some embodiments, these systems can be relatively small in size to be portable such that they can be utilized in the field for specific diagnostic testing applications. In some other embodiments, the systems can be configured for diagnostic testing in a laboratory setting.

Figure 1A:
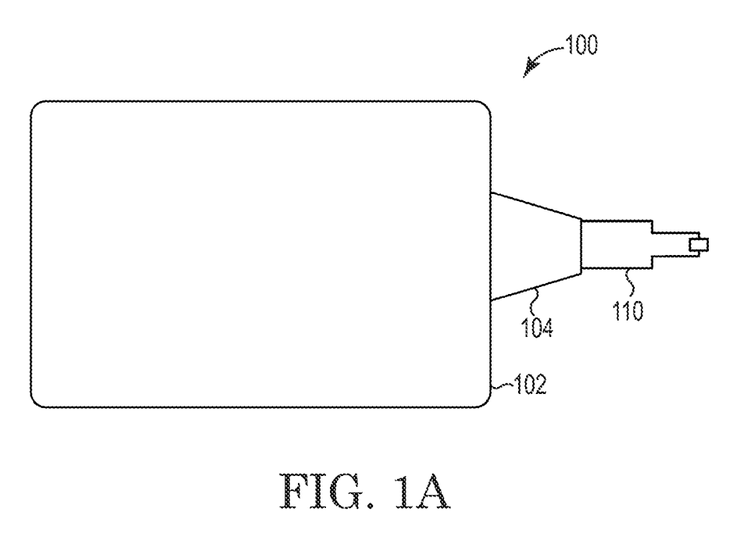
FIG. 1A is a schematic diagram of one embodiment of a resonator sensor system that includes a measurement apparatus and a resonator sensor module.
Figure 1B:
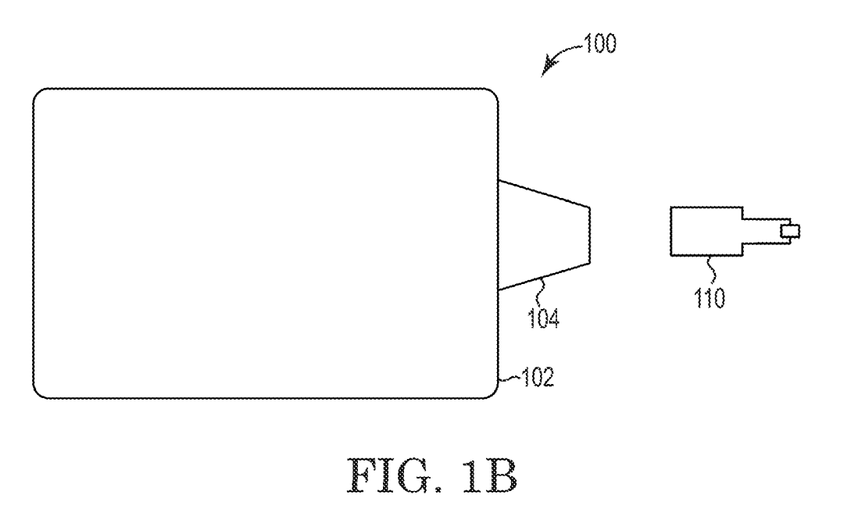
FIG. 1B is a schematic diagram of the system of FIG. 1A with the resonator sensor module detached from the measurement apparatus.

FIGS. 1A and 1B are schematic diagrams of resonator sensor system 100, which, in the illustrated embodiment, is a hand-held or portable system. The system 100 includes measurement apparatus 102 that is capable of being interfaced with a resonator sensor module 110 by an interconnector 104. The system 100 can be used for point of need diagnostic testing in the field. Although the system 100 is depicted as being portable, in some embodiments, the system can be utilized on a laboratory bench or in a more permanent configuration. Although not shown in FIGS. 1A-B, the system 100 can include devices and circuitry for connection to the internet or otherwise transferring information, such as one or more USB ports, wireless connection, or the like.

In some embodiments, the interconnector 104 can contain a data storage device such as a ROM or flash EEPROM. The data storage device may serve to set up the instrument for specific market applications by including software or identification information that allows the instrument to understand the particular use of the system 100 as it relates to the resonator sensor module 110. For instance, the read-only memory may contain basic information or algorithmic instructions for the interpretive logic of the instrument that relates to the output signal of the module 110, which may serve to limit the system 100 to specific applications, such as limited only to use in one of: veterinary applications, toxicology applications, drugs of abuse applications; GMO grain applications, for example.

The data storage device can also contain sensor-type specific information such as the general frequency range or approximate resonance frequency of one or more resonators of the module 110 as determined during post-production testing. This information could, for example, reduce sensor detection and calibration setup time when a new sensor is coupled to an instrument. In a related embodiment, the data storage device contains lookup tables of calibration correction constants that are indexed by lookup codes individually determined for the sensors at the factory. In various other embodiments, the lookup code may be supplied via printed label, barcode label, or using a RFID tag.

In some embodiments, the module 110 can include a read-only memory (ROM) or small flash device having its own specific calibration constants specific to the individual sensor module. This data could be supplied based on factory calibration performed on a representative sample taken from the manufactured lot in which the individual module 110 was fabricated.

In some embodiments, the system 100 is configured with a network interface device and associated firmware/drivers, which enable the system to automatically initiate a query over a network to obtain calibration constants for the specific sensor module. This embodiment eliminates the need for maintaining calibration data locally. Instead, when a new resonator sensor module is attached, the instrument determines the serial number associated with the particular sensor module (using RFID, bar code scanning, etc.), and uses that information to form its query. The database having specific sensor calibration data may be stored on a server located at the laboratory facility, or remotely (e.g., at the manufacturer's facility), in which case the network over which the query is placed is a wide area network (WAN) such as the Internet.

Resonator sensor module 110 includes one or more resonators such as bulk acoustic wave devices, for instance, described in greater detail herein. In various embodiments, module 110 may or may not include circuitry that interfaces with the one or more resonators. For instance, in some embodiments, actuation circuitry that is configured to drive one or more sensing resonators and one or more reference resonators into an oscillating motion can be incorporated into the module 110. In some embodiments, measurement circuitry, including analog-to-digital conversion, that is configured to measure one or more resonator output signals representing a resonance characteristic of the oscillating motion of the one or more sensing resonators and the one or more reference resonators can also be incorporated into the module 110. In some embodiments, the actuation and/or measurement circuitry are provided in measurement apparatus 102.

Figure 3:
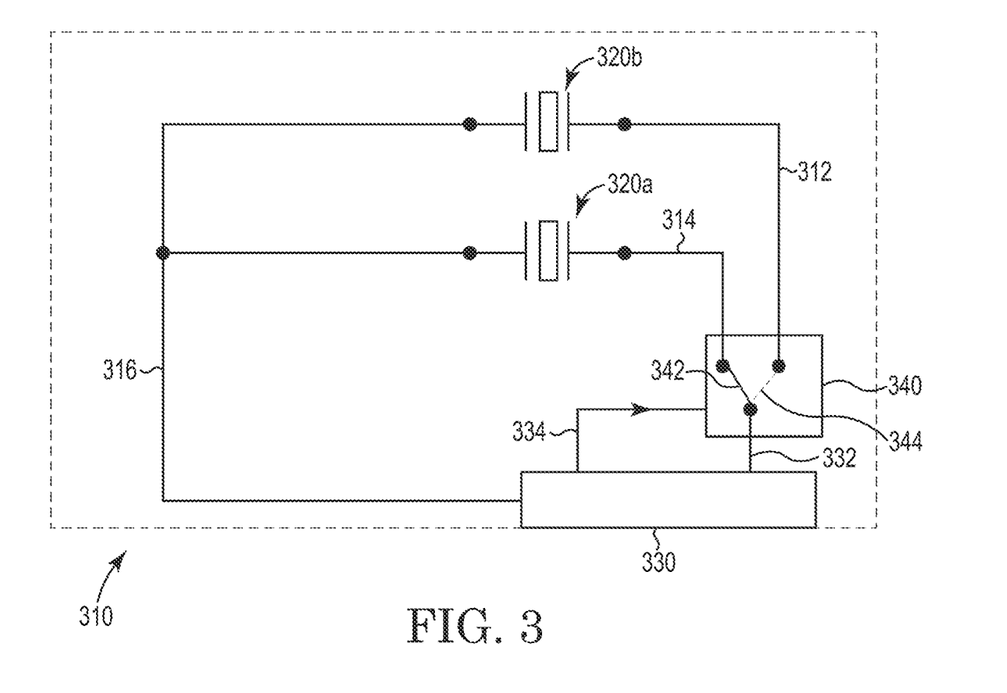
FIG. 3 is a schematic diagram of one embodiment of a resonator sensor module.

The resonator sensor module 110 can be operatively connected to the measurement apparatus 102 via interconnector 104 and a module interface (e.g., interface 330 of FIG. 3). Once detection and testing is completed, the module 110 can be detached from apparatus 102 and either reconditioned for additional testing or disposed of.

Figure 2A:
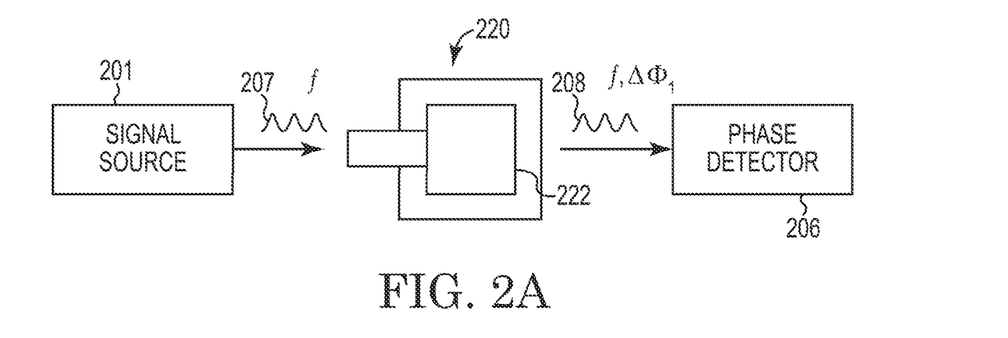
FIGS. 2A-C are schematic diagrams illustrating the operational principles of embodiments of resonator sensor systems.
Figure 2B:
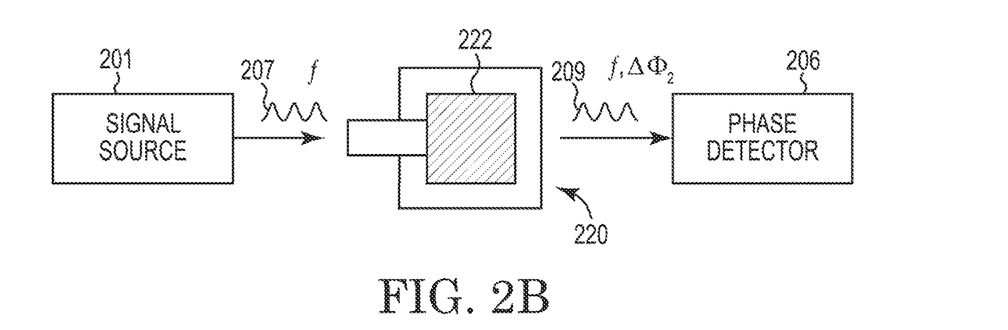

Any suitable techniques can be used with the system 100 of FIGS. 1A-B for detection of test material. For example, FIGS. 2A and 2B illustrate general operating principles of a bulk-acoustic wave piezoelectric resonator 220 used as a sensor to detect an analyte. Such resonators may be included in the resonator sensor modules described herein, e.g., module 110. The resonator 220 typically includes a planar layer of piezoelectric material bounded on opposite sides by two respective metal layers that form the electrodes of the resonator. The two surfaces of the resonator are free to undergo vibrational movement when the resonator is driven by a signal within the resonance band of the resonator. When the resonator 220 is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion phase shift of the resonator caused by the binding of the material being detected on the surface of the resonator. Such sensors differ from those that operate the resonator as an oscillator and monitor changes in the oscillation frequency. Rather, such sensors insert the resonator in the path of a signal of a pre-selected frequency and monitor the variation of the insertion phase shift caused by the binding of the material being detected on the resonator surface.

In more detail, FIG. 2A shows the resonator 220 before the material being detected is bound to its surface 222. The depicted resonator 220 is electrically coupled to a signal source 201, which provides an input signal 207 having a frequency f within the resonance band of the resonator. The input electrical signal 207 is coupled to the resonator 220 and transmitted through the resonator to provide a resonator output signal 208. In some embodiments, the output signal 208 is at the same frequency as the input signal 207, but differs in phase from the input signal by a phase shift $\phi_1$, which depends on the piezoelectric properties and physical dimensions of the resonator. The output signal 208 is coupled to a phase detector 206 that provides a phase signal related to the insertion phase shift.

FIG. 2B shows the resonator 220 with the material being detected bound on its surface 222. The same input signal 207 is coupled to the resonator 220. Because the resonant characteristics of the resonator 220 are altered by the binding of the material as a perturbation, the insertion phase shift of the output signal 209 is changed to $\phi_2$. The change in insertion phase shift caused by the binding of the material is detected by the phase detector 206. The measured phase shift change is related to the amount of the material bound on the surface of the resonator.

Figure 2C:
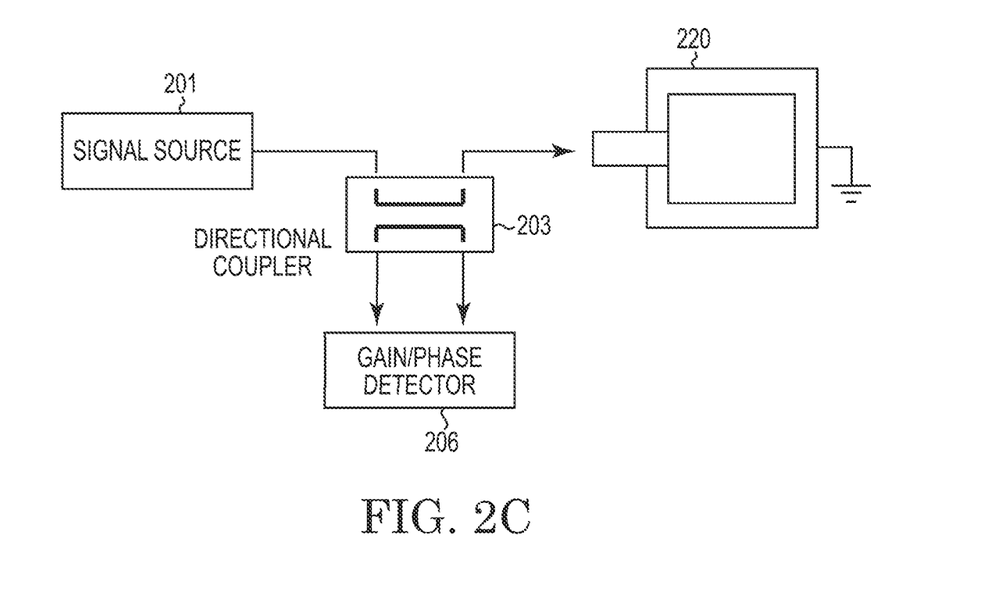

FIG. 2C shows an alternative to measuring the insertion phase of the resonator. A directional coupler 203 is added between the signal source 201 and the resonator 220 with the opposite electrode grounded. The phase detector 206 is configured to measure the phase shift of the reflection coefficient as a result of material binding to the resonator surface.

This phase detection approach can be advantageously used with piezoelectric resonators of different resonant frequencies, e.g., frequencies of about 500 MHz or greater, such as about 700 MHz or greater, about 900 MHz or greater, about 1 MHz or greater, 1.5 GHz or greater, about 1.8 GH or greater, about 2 GHz or greater, 2.2 GHz or greater, 2.5 GHz or greater, about 3 GHZ or greater, or about 5 GHZ or greater. In embodiments, the piezoelectric resonators have resonance frequencies of from about 500 MHz to about 5 GHz, such as from about 900 MHz to about 3 GHz, or from about 1.5 GHz to about 2.5 GHz.

The resonators described herein are thin-film resonators. Thin film resonators include a thin layer of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. In some embodiments, thin-film resonators may be preferred because of their high resonance frequencies and the theoretically higher sensitivities. Depending on the applications, a thin-film resonator can be formed to support either longitudinal or shear bulk-acoustic wave resonant modes. In some embodiments, the resonator is formed to support shear bulk-acoustic wave resonant modes, as they can be more suitable for use in a liquid sample.

Additional details regarding sensor devices and systems that may employ TFRs are described, for example, in U.S. Pat. No. 5,932,953 issued Aug. 3, 1999 to Drees et al., entitled METHOD AND SYSTEM FOR DETECTING MATERIAL USING PIEZOELECTRIC RESONATORS; and U.S. Pat. No. 8,409,875 issued Apr. 2, 2013, to Johal et al., entitled MEASUREMENT OF BINDING KINETICS WITH A RESONATING SENSOR.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate ($LiTaO_3$), lithium niobate ($LiNbO_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

One or more resonators can be provided or formed on a substrate with other devices to provide a resonator sensor module. For example, FIG. 3 is a schematic diagram of one embodiment of a resonator sensor module 310. As illustrated in FIG. 3, the module 310 includes resonators 320a and 320b, a module interface 330, and a switch 340. The switch 340 includes a first position 342 that operatively couples resonator 320a to the module interface 330, and a second position 344 that operatively couples resonator 320b to the module interface.

Resonators 320a-b can include any suitable resonators, e.g., surface acoustic wave, shear-mode acoustic wave, flexural plate wave, bulk acoustic wave, or shear-mode bulk acoustic wave resonators. In some embodiments, resonator 320a may be a sensing resonator that includes binding sites for an analyte material, and resonator 320b may be a reference resonator that lacks any binding sites for the analyte material. And although only two resonators 320a-b are illustrated in the FIG. 3, some embodiments may include three, four, five, or more resonators. In such embodiments, one or more sensing resonators and one or more reference resonators may be included as is further described herein.

In some embodiments, the module 310 can include one or more printed circuit boards (PCBs), with one or more resonators mounted thereon. The close proximity of two or more resonators can ensure that the resonators are subjected to substantially identical environmental conditions during a material sensing operation. The use of one or more sensing resonators and one or more reference resonators can provide more accurate resonance shift measurements and cancellation of environmental effects during material sensing operations.

In some embodiments, module 310 can include back-to-back PCB configurations utilizing two substantially different PCBs. In one approach, the resonator on one PCB is situated off-center while the resonator on the other PCB is centered. In this configuration, the reference and sensing resonators can still have sufficient distance there-between to reduce cross talk between the two resonators. In another aspect of the present disclosure, the resonators on the two PCBs are constructed such that the back-to-back PCB configuration results in the reference and sensing resonators being directly opposed.

In some embodiments, the sensing resonator is coated with a different material than a reference resonator depending upon the material to be detected. By varying the coating on the resonators, the disclosed systems can allow universal use for various diagnostic testing of chemical and/or biological materials without changing any of the other system structural components. Sensors for resonance shift detection of chemical and/or biological materials effectively allow fast response times for the detection of the respective chemical and/or biological material, in the field detection capabilities, small sample sizes, minimally trained individuals, low direct and indirect costs, and electronically transmittable data.

Figure 5:
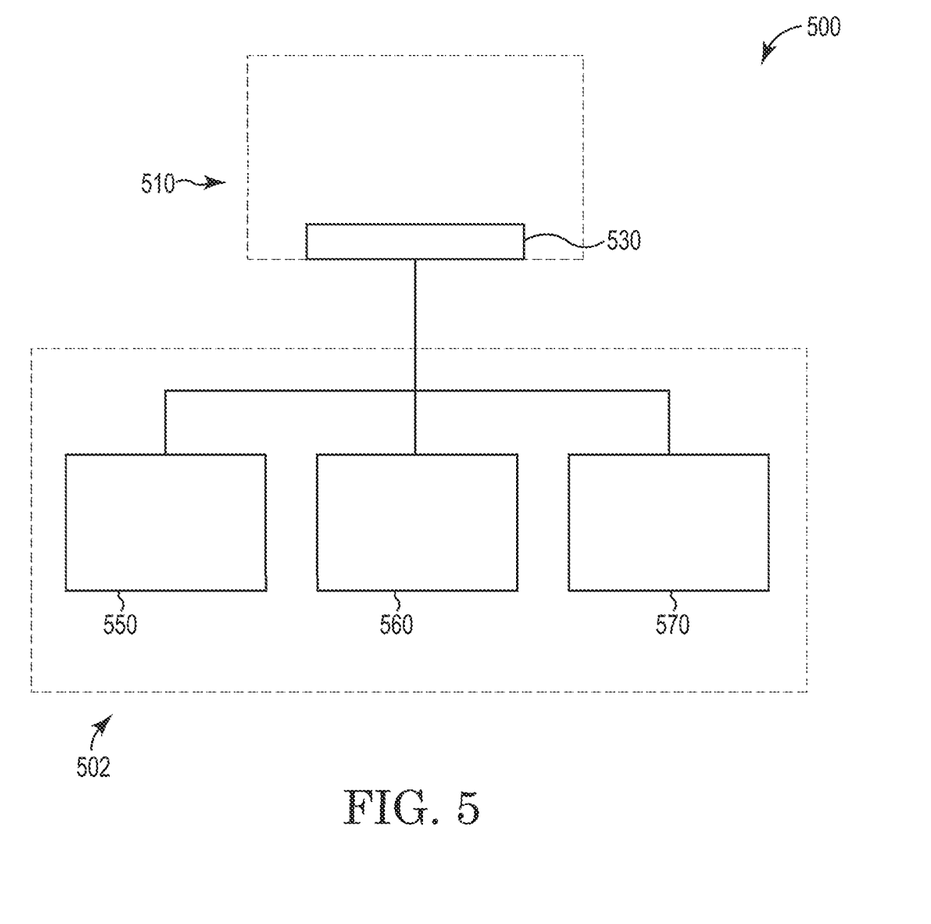
FIG. 5 is a schematic diagram of another embodiment of a resonator sensor system.

Returning to FIG. 3, the module interface 330 can include any suitable interface for operatively coupling or connecting the resonator sensor module 310 to another device, e.g., measurement apparatus 502 of FIG. 5 as is further described herein. In general, the module interface 330 can include any suitable connectors that can provide electrical, optical, or other types of coupling to another device. The module interface 330 may be configured in any suitable manner and include any suitable number of connections or terminals. In some embodiments, the module interface 330 can include a plurality of contacts. The module interface 330 can also be configured to couple the module 310 to ground.

The resonator sensor module 310 of FIG. 3 also includes one or more switches 340. Although FIG. 3 includes a single switch 340, the module 310 can include any suitable number of switches. Further, the switch 340 may include any suitable type of switch or switches, e.g., reflective multiport microwave switches, radio-frequency switches, PIN diodes, absorptive or reflective mechanical switches, absorptive or reflective PIN diode switches, absorptive or reflective FET or BJT switches, RFIC based absorptive or reflective switches, multiplexers, or combinations thereof.

In some embodiments, the switch 340 can be controlled by a controller (e.g., controller 570 of FIG. 5) or other suitable device such that it can be positioned in the first position 342 or the second position 344. Such a controller can direct one or more signals to the switch 340 through the module interface 330 and transmission line 334. Although illustrated as having first and second positions 342, 344, the switch 340 can include any suitable number of positions, e.g., three or more positions.

The first position 342 of switch 340 operatively couples resonator 320a and the module interface 330, and the second position 344 operatively couples resonator 320b and the module interface. For example, in some embodiments, the first position 342 operatively couples resonator 320a and the module interface 330 such that energy (e.g., electrical energy) can flow between the resonator and module. Such coupling takes place through transmission lines 332 and 314. Whereas when the switch is in the second position 344, the resonator 320b is operatively coupled to the module interface 330 via transmission line 332 and transmission line 312 such that energy can flow between the resonator and module. Energy can then be directed from one or both of the resonators 320a-b through transmission line 316 back to module interface 330.

The resonator sensor module 310 can be provided or formed on any suitable substrate or substrates, e.g., rigid or flexible organic PCB (epoxy glass, polyamide, Cyanite Ester, Nylon, TEFLON) or ceramic substrates (Alumina, Sapphire, Silicon, glass). and combinations thereof. The resonators 320a-b, the switch 340, the module interface 330, and the transmission lines 312, 314, 316, 332, and 334 can be formed on a substrate using any suitable technique or techniques.

In some embodiments, the resonator module 310 can include other suitable devices, e.g., actuation circuitry 550 and measurement circuitry 560 of FIG. 5. In other embodiments, the resonator sensor module 310 includes electrical components consisting essentially of: one or more sensing resonators 320a, one or more reference resonators 320b, the module interface 330, and one or more switches 340.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

"Consisting essentially of", as it relates to a compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods.

Figure 4:
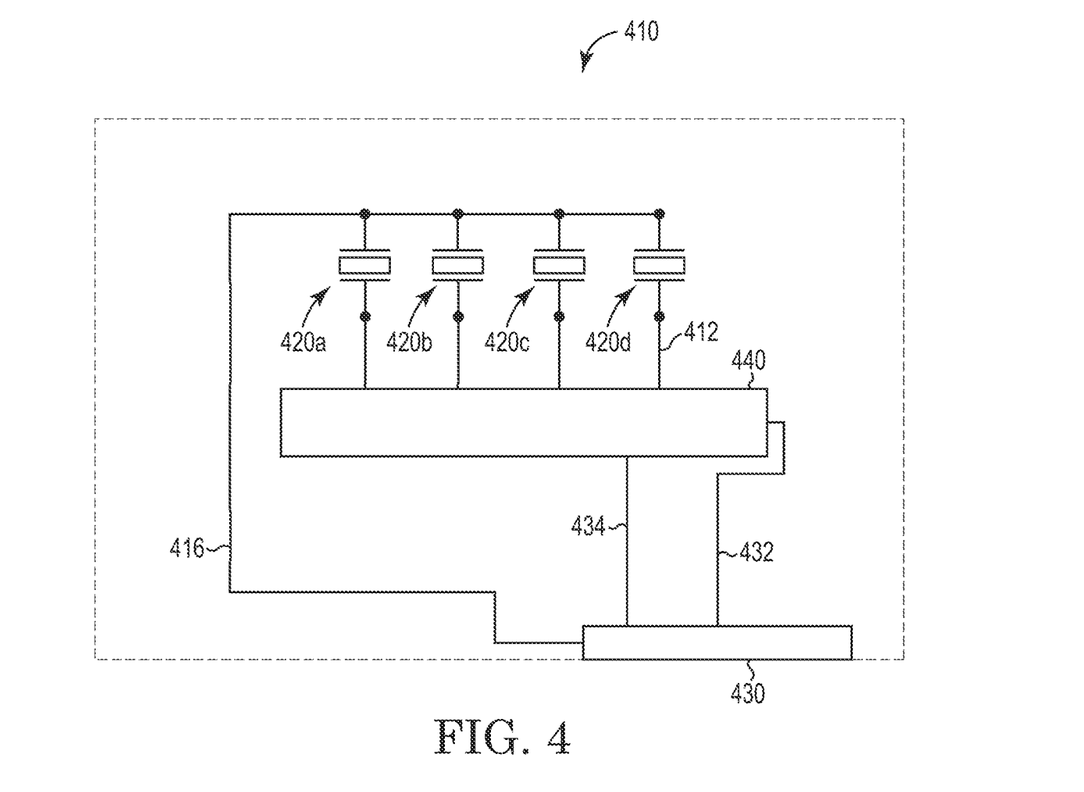
FIG. 4 is a schematic diagram of another embodiment of a resonator sensor module.

As mentioned herein, the resonator sensor modules of the present disclosure can include any suitable number of resonators. For example, FIG. 4 is a schematic diagram of an embodiment of a resonator sensor module 410 that includes four resonators 420a-d. The module 410 also includes a module interface 430, and a switch 440 that operatively couples the resonators 420a-d to the module interface. All of the design considerations and possibilities regarding the resonators 320*a-b*, the module interface 330, and the switch 340 of the module 310 of FIG. 3 apply equally to the resonators 420*a-d*, the module interface 430, and the switch 440 of the resonator sensor module 410 of FIG. 4.

One or more of the resonators 420*a-d* can include a sensing resonator, and one or more can include a reference resonator. Although the module 410 includes resonators 420*a-d* in a parallel configuration, any suitable configuration can be utilized. Further, in some embodiments, the resonators 420*a-d* can be provided in pairs such that a sensing resonator is paired with a reference resonator.

To accommodate the increased number of resonators 420*a-d*, the switch 440 can be a multiplexer that is operable to couple one or more of the resonators with the module interface 430 based upon a control signal or signals provided, e.g., by a controller (e.g., controller 570 of FIG. 5) as is further described herein.

The various embodiments of resonator sensor modules described herein can be used with any suitable measurement apparatus to provide a resonator sensor system for measuring the binding kinetics of an interaction of an analyte material present in a fluid sample, e.g., the apparatuses described in U.S. Pat. No. 8,409,875. For example, FIG. 5 is a schematic diagram of one embodiment of a system 500 that includes a resonator sensor module 510 and a measurement apparatus 502. The resonator sensor module 510 can include any resonator sensor module described herein, e.g., module 310 of FIG. 3. Module 510 includes a module interface 530. All of the design considerations and possibilities regarding the module interface 330 of FIG. 3 apply equally to the module interface 530 of FIG. 5.

As illustrated, the measurement apparatus 502 is operatively coupled to the resonator sensor module 510 through the module interface 530. Although not shown, the measurement apparatus 502 can include any suitable interface for operatively connecting the apparatus to the module interface 530 (e.g., interconnector 104 of FIGS. 1A-B).

The apparatus 502 includes actuation circuitry 550, measurement circuitry 560, and a controller 570 operatively coupled to the actuation and measurement circuitry.

The actuation circuitry 550 is configured to drive the resonators (e.g., resonators 320*a-b* of FIG. 3) of the module 510 into an oscillating motion as is further described herein. The actuation circuitry 550 can include any suitable device or devices to drive the resonators in this manner, e.g., synthesizers, independent current sources, independent voltage sources, voltage controlled oscillators (VCO), backward wave oscillators (BWO), and combinations thereof.

The actuation circuitry 550 is configured to drive the one or more resonators at any suitable frequency or frequencies. In some embodiments, the actuation circuitry 550 is configured to drive one or more resonators at its resonant frequency. In some embodiments, the actuation circuitry 550 is configured to drive one resonator at a first frequency and a second resonator at a second frequency. For example, the resonator sensor module 510 can include one or more sensing resonators and one or more reference resonators. The actuation circuitry 550 would, therefore, be configured to drive the one or more sensing resonators at a first frequency and the one or more reference resonators at a second frequency. In some embodiments, the first frequency is substantially equal to the second frequency. In other embodiments, the first frequency is different from the second frequency.

The system 500 also includes measurement circuitry 560 configured to measure one or more resonator output signals representing a resonance characteristic of the oscillating motion of the one or more resonators of module 510. Measurement circuitry 560 can include any suitable device or devices to measure these output signals, e.g., gain/phase detectors, amplifiers, filters, analog-to-digital circuits (ADCs), digital-to-analog circuits (DACs), mixers, directional couplers, RF receivers, and combinations thereof.

Also included in the measurement apparatus 502 of the embodiment illustrated in FIG. 5 is a controller 570. The controller 570 is operatively coupled to the actuation circuitry 550 and measurement circuitry 560. The controller 570 can include any suitable device or devices, e.g., microprocessors, microcontrollers, field programmable gate arrays (FPGAs), analog control circuits, application specific integrated circuits (ASICs), computers, and combinations thereof. In some embodiments, the controller 570 can include a combination of hardware and software, such as by a microprocessor system and a set of instructions to implement the controller's functionality. In other embodiments, the controller 570 can be implemented as a combination of the two, with certain functions facilitated by hardware alone, and other functions facilitated by a combination of hardware and software. A variety of suitable microprocessor systems may be utilized including, without limitation, one or more microcontrollers, one or more digital signal processors, and the like, along with appropriate interfacing circuitry, data storage, power conditioning system, etc., as needed to implement the controller's functionality.

In some embodiments, the controller 570 is configured to perform various measurement functions as are described further in U.S. Pat. Nos. 5,932,953 and 8,409,875. For example, in some embodiments, the controller 570 is configured to detect introduction of a fluid sample into contact with at least one of the one or more sensing resonators of module 510 based on detection of a characteristic change in the sensing resonator output signal, e.g., the resonant frequency of the one or more sensing resonators. And in some embodiments, the controller 570 is configured, in response to the detection of the introduction of the fluid sample, to initiate measurement of the binding kinetics of the analyte material to the at least one of the one or more sensing resonators.

In some embodiments, the controller 570 is further configured to monitor the one or more resonator output signals from a time reference based on the time of occurrence of the characteristic change in the output signal. Further, in some embodiments, the controller 570 is configured to detect a step change in a resonant characteristic of at least one of the one or more sensing resonators and at least one of the one or more reference resonators selected from the group consisting of: a frequency, a reflection or transmission phase angle, a reflection or transmission amplitude, or any combination thereof. And in some embodiments, the controller 570 is further configured to determine a measure of concentration of the analyte in the fluid sample based on the binding kinetics.

The controller 570 is further configured to send a control signal to the switch (e.g., switch 340 of FIG. 3) to position the switch in either a first position or a second position. The control signal is provided to the switch via the module interface 530.

Any suitable technique or techniques may be utilized with the system 500 and the disclosed resonator sensor modules for measuring binding kinetics of an interaction of an analyte material present in a fluid sample, e.g., the techniques described in U.S. Pat. Nos. 5,932,953 and 8,409,875. For example, one exemplary technique is described with reference to resonator sensor module 310 of FIG. 3 and system 500 of FIG. 5. Such a technique can include providing a resonator sensor module 310 that includes one or more sensing resonators 320a, one or more reference resonators 320b, a module interface 330, and one or more switches 340. In some embodiments, the one or more sensing resonators 320a can include binding sites for the analyte material, and the one or more reference resonators 320b lack any binding sites for the analyte. The one or more switches 340 can be positioned in a first position 342 by controller 570 such that the one or more sensing resonators 320a is operatively coupled to the module interface 530.

Prior to exposing the one or more sensing resonators 320a and the one or more reference resonators 320b to the fluid sample, the one or more sensing resonators can be activated via the module interface 330 such that the one or more sensing resonators produces at least one sensor output signal representing a resonance characteristic of the one or more sensing resonators. In some embodiments, the one or more sensing resonators 320a and the one or more reference resonators 320b can be operated at their corresponding resonant frequencies, which are potentially different from one another, using actuation circuitry 550.

The introduction of a fluid sample to the one or more sensing resonators 320a based on detection of a characteristic change in the at least one sensor output signal can be automatically detected using measurement circuitry 560 and controller 570. Any suitable characteristic change can be detected to determine the introduction of a fluid sample, e.g., a frequency, a transmission or reflection phase angle, a transmission or reflection amplitude, or any combination thereof.

The switch 340 can then be positioned in a second position 344 by controller 570 such that the one or more reference resonators 320b is operatively coupled to the module interface 330. Operation of the one or more reference resonators 320b is initiated via the module interface 330 such that the one or more reference resonators produces at least one reference output signal representing a resonance characteristic of the one or more reference resonators.

In response to the detecting of the introduction of the fluid sample, automated measurement of the binding kinetics of the analyte material to the sensing resonator is initiated by the controller 570. In some embodiments, initiating the automated measurement of the binding kinetics can include monitoring of the at least one sensor output signal and at least one reference signal from a time reference based on the time of occurrence of the characteristic change in the at least one sensor output signal. In some embodiments, a total amount of change of the at least one sensor output signal time-referenced from the detection of the characteristic change in the at least one sensor output signal can be automatically measured. Further, in some embodiments, a degree of the characteristic change in the at least one sensor output signal can be compared against a threshold value or target range of values such that false detections are suppressed to automatically detect introduction of a fluid sample to the one or more sensing resonators 320a.

In some embodiments, a measure of concentration of the analyte in the fluid sample can be determined by the controller 570 based on the binding kinetics.

Figure 6:
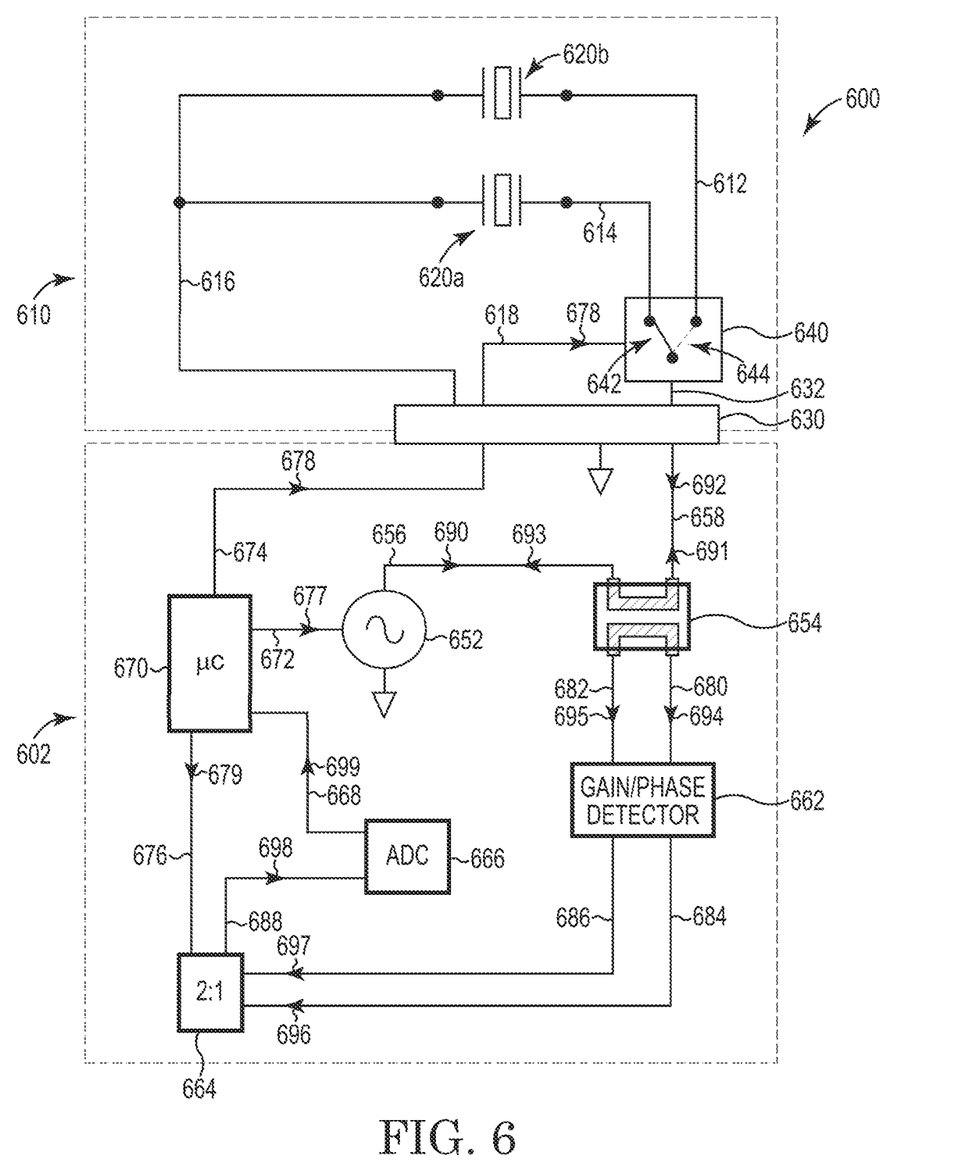
FIG. 6 is a schematic diagram of another embodiment of a resonator sensor system.

As mentioned herein, the actuation circuitry, measurement circuitry, and controller of the measurement apparatus can include any suitable device or devices to measure desired characteristics of the resonators. For example, FIG. 6 is a schematic diagram of one exemplary embodiment of a resonator sensor system 600 that includes a resonator sensor module 610 and a measurement apparatus 602. The resonator sensor module 610 includes resonators 620a-b, a module interface 630, and a switch 640. All of the design considerations and possibilities regarding the resonator sensor module 310 of FIG. 3 apply equally to the resonator sensor module 610 of FIG. 6.

Measurement apparatus 602, which is operatively coupled to resonator sensor module 610 through the module interface 630, includes actuation circuitry configured to drive the resonators 620a-b into an oscillating motion, measurement circuitry configured to measure one or more resonator output signals representing a resonance characteristic of the oscillating motion of the resonators, and a controller 670 operatively coupled to the actuation and measurement circuitry. All of the design possibilities and considerations regarding the measurement apparatus 502 of FIG. 5 apply equally to the measurement apparatus 602 of FIG. 6.

In the embodiment illustrated in FIG. 6, the actuation circuitry includes synthesizer 652, which is operatively coupled to controller 670 via data bus 672. Any suitable synthesizer may be utilized for synthesizer 652. In some embodiments, the actuation circuitry can include any suitable energy source that is capable of driving the resonators 620a-b into an oscillatory motion as described herein. Further, the actuation circuitry can include other suitable devices that aid in driving the resonators 620a-b into an oscillating motion, e.g., synthesizers, independent current sources, independent voltage sources, voltage controlled oscillators (VCOs), backward wave oscillators (BWOs), and combinations thereof.

The measurement circuitry of apparatus 602 includes a gain/phase detector 662 operatively coupled to multiplexer 664 via signal line 684 and 686. The multiplexer 664 is operatively coupled to ADC 666 via signal line 688 and to controller 670 via data line 676. And the ADC 666 is operatively coupled to controller 670 via data bus 668. Measurement circuitry can include any suitable devices that aid in measuring one or more resonator output signals representing a resonance characteristic of the oscillating motion of the resonators 620a-b, e.g., gain/phase detectors, amplifiers, filters, analog-to-digital circuits (ADCs), digital-to-analog circuits (DACs), mixers, directional couplers, RF receivers, and combinations thereof.

Although not shown, measurement apparatus 602 can include any suitable interface that operationally couples the apparatus 602 to the module interface 630 of resonator sensor module 610, e.g., interconnector 104 of FIGS. 1A-B.

In one exemplary embodiment, the controller 670, which is operatively coupled to the actuation and measurement circuitry, sends a control signal 677 on line 672 to synthesizer 652 to provide a characteristic change in at least one sensor output signal to be measured. The synthesizer 652 generates a first input signal 690 on line 656 that is directed to directional coupler 654. Any suitable coupler or couplers may be utilized for directional coupler 654.

At least a portion of the first input signal 690 passes through directional coupler 654 to provide a second input signal 691 on line 658 that is directed to module interface 630. The module interface 630 in turn directs the second input signal 691 to switch 640 along line 632. The switch 640 is configured to operatively couple the module interface 630 to resonator 620a via transmission line 614 when the switch is in a first position 642. When the switch 640 is in a second position 644, the module interface 630 is operatively coupled to resonator 620b via transmission line 612. The controller 670 directs a control signal 678 along line 678 to the module interface 630, which then directs the control signal along line 618 to the switch 640 to position the switch in either the first position 642 or the second position 644.

When switch 640 is in the first position 642, the second input signal 691 is transmitted to resonator 620a. In some embodiments, the second input signal 691 is provided to drive the resonator 620a into an oscillating motion at a first frequency.

A first resonator output signal 692 that represents a resonance characteristic of the resonator 620a is transmitted on transmission line 658.

At least a portion of the first resonator output signal 692 passes through directional coupler 654 and onto transmission line 656 to provide a second resonator output signal 693 to synthesizer 652. The directional coupler 654 directs a portion of the first input signal 690 onto transmission line 682 to provide a third input signal 695 that is directed to gain and phase detector 662. Additionally, the directional coupler 654 directs at least a portion of the first resonator output signal 692 from resonator 620a onto transmission line 680 to provide a third resonator output signal 694 that is directed to gain and phase detector 662.

The gain and phase detector 662 is operable to generate and then transmit a first analog signal 696 on line 684 and a second analog signal 697 on line 686. The first analog signal 696 is proportional to a first characteristic difference (e.g., phase difference) between the third resonator output signal 694 and third input signal 695. The second analog signal 697 is proportional to a second characteristic difference between the third resonator output signal 694 and third input signal 695, e.g., a magnitude ratio.

The first analog signal 696 and second analog signal 697 are directed to analog inputs of multiplexer 664. Multiplexer 664 also receives a control signal 679 on line 676 from controller 670 such that the multiplexer output signal 698 on line 688 is equal to one of the analog signals 696, 697, depending upon the control signal 679.

The controller 670 generates the control signal 679 to select which of the analog signals 696, 697 are relayed to ADC 666. The ADC 666 converts the analog signal 698 to a digital signal 699 and directs it to controller 670 along line 668.

The controller 670 directs another control signal 678 through module interface 630 to switch 640 to position the switch in the second position 644, and the process of actuating resonator 620b and measuring at least one reference output signal that represents a resonance characteristic of the resonator 620b can be performed in a manner similar to the process described for actuating and measuring resonator 620a. Further, one or both of resonators 620a-b can be actuated and measured numerous times to aid in measuring the binding kinetics of an interaction of an analyte material present in a fluid sample.

In this manner, the controller 670 specifies a measurement signal configuration (e.g., frequency, power output level, etc.), and collects the digital signals representing the characteristic change in the sensor output signal for resonators 620a-b. For example, in some embodiments, the incident phase relative to reflected phase and incident magnitude relative to reflected magnitude are detected to provide measurements for resonators 620a-b. In some embodiments, the controller 670 will sequence through a range of frequency settings and collect reflection coefficients at each frequency for each resonator 620a-b. From these reflection coefficients over a frequency range spanning resonance for resonators 620a-b, the resonant characteristics for the resonators can be quantified.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method for measuring binding kinetics of an interaction of an analyte material present in a fluid sample, the method comprising:
   providing a resonator sensor module comprising one or more sensing resonators, one or more reference resonators, a module interface, and a switch, wherein the one or more sensing resonators comprises binding sites for the analyte material and the one or more reference resonators lacks any binding sites for the analyte;
   positioning the switch in a first position such that the one or more sensing resonators is operatively coupled to the module interface;
   prior to exposing the one or more sensing resonators and the one or more reference resonators to the fluid sample, initiating operation of the one or more sensing resonators via the module interface such that the one or more sensing resonators produces at least one sensor output signal representing a resonance characteristic of the one or more sensing resonators;
   automatically detecting introduction of a fluid sample to the one or more sensing resonators based on detection of a characteristic change in the at least one sensor output signal;
   positioning the switch in a second position such that the one or more reference resonators is operatively coupled to the module interface;
   initiating operation of the one or more reference resonators via the module interface such that the one or more reference resonators produces at least one reference output signal representing a resonance characteristic of the one or more reference resonators; and
   in response to the detecting of the introduction of the fluid sample, initiating automated measurement of the binding kinetics of the analyte material to the one or more sensing resonators.

2. The method of claim 1, wherein initiating the automated measurement of the binding kinetics comprises monitoring of the at least one sensor output signal and at least one reference output signal from a time reference based on the time of occurrence of the characteristic change in the at least one sensor output signal.

3. The method of claim 1, wherein the detection of the characteristic change in the at least one sensor output signal comprises detection of a step change in a resonant characteristic of the one or more sensing resonators selected from the group consisting of: a frequency, a transmission or reflection phase angle, a transmission or reflection amplitude, or any combination thereof.

4. The method of claim 1, wherein initiating automated measurement of the binding kinetics comprises measuring a total amount of change of the at least one sensor output signal time-referenced from the detection of the characteristic change in the at least one sensor output signal.

5. The method of claim 1, further comprising operating each of the one or more sensing resonators and the one or more reference resonators at their corresponding resonant frequencies, which are potentially different from one another.

6. The method of claim 1, further comprising determining a measure of concentration of the analyte in the fluid sample based on the binding kinetics.

* * * * *